United States Patent
Peters

(10) Patent No.: US 9,555,493 B2
(45) Date of Patent: Jan. 31, 2017

(54) APPARATUS FOR WELDING WITH CURTAIN ELECTRODES AND STRIP ELECTRODES

(75) Inventor: Steven Peters, Huntsburg, OH (US)

(73) Assignee: LINCOLN GLOBAL, INC., City of Industry, CA (US)

( * ) Notice: Subject to any disclaimer, the term of this patent is extended or adjusted under 35 U.S.C. 154(b) by 987 days.

(21) Appl. No.: 12/983,157

(22) Filed: Dec. 31, 2010

(65) Prior Publication Data

US 2011/0168676 A1    Jul. 14, 2011

(51) Int. Cl.
| | |
|---|---|
| B23K 9/04 | (2006.01) |
| A61B 10/00 | (2006.01) |
| A61B 10/02 | (2006.01) |
| B23K 9/09 | (2006.01) |
| B23K 9/10 | (2006.01) |
| B23K 9/173 | (2006.01) |
| B23K 9/18 | (2006.01) |
| B23K 25/00 | (2006.01) |

(52) U.S. Cl.
CPC ........... *B23K 9/042* (2013.01); *A61B 10/0045* (2013.01); *A61B 10/02* (2013.01); *B23K 9/09* (2013.01); *B23K 9/1043* (2013.01); *B23K 9/1735* (2013.01); *B23K 9/188* (2013.01); *B23K 25/00* (2013.01); *A61B 10/0283* (2013.01); *A61B 2010/008* (2013.01)

(58) Field of Classification Search
USPC ... 219/73, 73.1, 73.11, 81, 83, 84, 123, 128, 219/137 P, 137 R, 137.2
See application file for complete search history.

(56) References Cited

U.S. PATENT DOCUMENTS

| | | | |
|---|---|---|---|
| 2,866,079 A | 12/1958 | Morley et al. | |
| 3,624,345 A | 11/1971 | Armstrong | |
| 3,694,620 A | 9/1972 | Gleason | |
| 3,882,298 A * | 5/1975 | Neff et al. | 219/73.21 |
| 4,437,906 A | 3/1984 | Tateishi et al. | |
| 5,324,552 A | 6/1994 | Opower et al. | |
| 5,714,735 A | 2/1998 | Offer | |
| 5,981,906 A | 11/1999 | Parker | |
| 6,069,334 A * | 5/2000 | Capitanescu | 219/61 |
| 6,172,333 B1 | 1/2001 | Stava | |
| 6,683,278 B2 * | 1/2004 | Stava et al. | 219/137 PS |
| 6,683,279 B1 | 1/2004 | Moerke | |
| 7,429,716 B2 | 9/2008 | Bong et al. | |

(Continued)

FOREIGN PATENT DOCUMENTS

| | | |
|---|---|---|
| DE | 2108614 A1 | 10/1971 |
| DE | 2445891 A1 | 4/1976 |

(Continued)

OTHER PUBLICATIONS

"Tandem Wire MIG Welding"; Wolf Robotics; Aug. 29, 2007.

(Continued)

*Primary Examiner* — Brian Jennison
(74) *Attorney, Agent, or Firm* — Perkins Coie LLP

(57) ABSTRACT

A system and method of welding is provided where a first welding power supply provides a first welding waveform to a strip electrode for welding a work piece and a second welding power supply provides a second welding waveform to at least one curtain electrode for welding the work piece. The at least one curtain electrode is positioned adjacent to a side of said strip electrode during welding.

9 Claims, 4 Drawing Sheets

(56) References Cited

U.S. PATENT DOCUMENTS

| | | |
|---|---|---|
| 7,495,192 B2 | 2/2009 | Takahashi et al. |
| 7,525,067 B2 | 4/2009 | Diez et al. |
| 2006/0070985 A1 | 4/2006 | Nakabayashi et al. |
| 2009/0050609 A1 | 2/2009 | Berger et al. |
| 2010/0213179 A1 | 8/2010 | Peters |
| 2010/0326963 A1 | 12/2010 | Peters et al. |
| 2011/0297658 A1 | 12/2011 | Peters et al. |
| 2013/0043219 A1 | 2/2013 | Peters et al. |
| 2013/0092667 A1 | 4/2013 | Peters et al. |

FOREIGN PATENT DOCUMENTS

| | | |
|---|---|---|
| DE | 19611583 A1 | 9/1997 |
| DE | 19611597 A1 | 9/1997 |
| DE | 102010018687 | 10/2011 |
| GB | 839203 A | 6/1960 |
| GB | 990208 A | 4/1965 |
| GB | 1502288 A | 3/1978 |
| GB | 2058637 A | 4/1981 |
| JP | 44-019978 | 8/1969 |
| JP | 54031748 B | 10/1979 |
| JP | 56-74373 A | 6/1981 |
| JP | 56-134067 | 10/1981 |
| JP | 2008055506 A | 3/2008 |
| JP | 2008087045 A | 4/2008 |
| JP | 2010069494 A | 4/2010 |
| JP | 2010082624 A | 4/2010 |
| SU | 1237347 A1 | 6/1986 |
| SU | 1602642 A1 | 10/1990 |

OTHER PUBLICATIONS

International Application No. PCT/IB2013/001460, International Search Report & Written Opinion, 10 pages, Jan. 15, 2015.
International Application No. PCT/IB2011/003065, International Search Report & Written Opinion, 5 pages, May 4, 2012.

* cited by examiner

US 9,555,493 B2

APPARATUS FOR WELDING WITH CURTAIN ELECTRODES AND STRIP ELECTRODES

BACKGROUND OF THE INVENTION

Field of the Invention

Devices, systems, and methods consistent with the invention relate to welding with cladding and curtain electrodes.

Description of the Related Art

Cladding with strip electrodes is known in the industry. Typically strip electrodes are used for cladding because of their large width and low penetration resulting in a large cladding area but low admixture with the base metal. This is especially true of electro-slag cladding. However, as the penetration is minimized, there is a risk of lack of penetration or even inclusions at the edges of the clad deposit especially where the deposit intersects with a previous adjacent deposit. If found, these inclusions require repair, if left unchecked, these inclusions can result in premature failure of the cladding layer. Further, when cladding with strip electrodes it is desirable to increase the width of the strip electrode to clad larger areas faster. However wider strip electrodes require significantly more current to apply. These high currents produce magnetic fields that become concentrated at the ends of the strip. These highly concentrated magnetic fields disturb the puddle and can force liquid metal from the edges of the weld deposit toward the center. In extreme cases, electro-magnetic steering devices are used to introduce a counter rotating magnetic fields to cancel some of the adverse affects of concentrated high magnetic fields at the edge of the strip electrode.

BRIEF SUMMARY OF THE INVENTION

An exemplary embodiment of the present invention is a welding system and method for welding which has a first welding power supply which provides a first welding waveform to a strip electrode for welding a work piece and a second welding power supply which provides a second welding waveform to at least one curtain electrode for welding the work piece. The at least one curtain electrode is positioned adjacent to a side of said strip electrode during welding.

BRIEF DESCRIPTION OF THE DRAWINGS

The above and/or other aspects of the invention will be more apparent by describing in detail exemplary embodiments of the invention with reference to the accompanying drawings, in which.

DETAILED DESCRIPTION OF EXEMPLARY EMBODIMENTS

Figure 1:
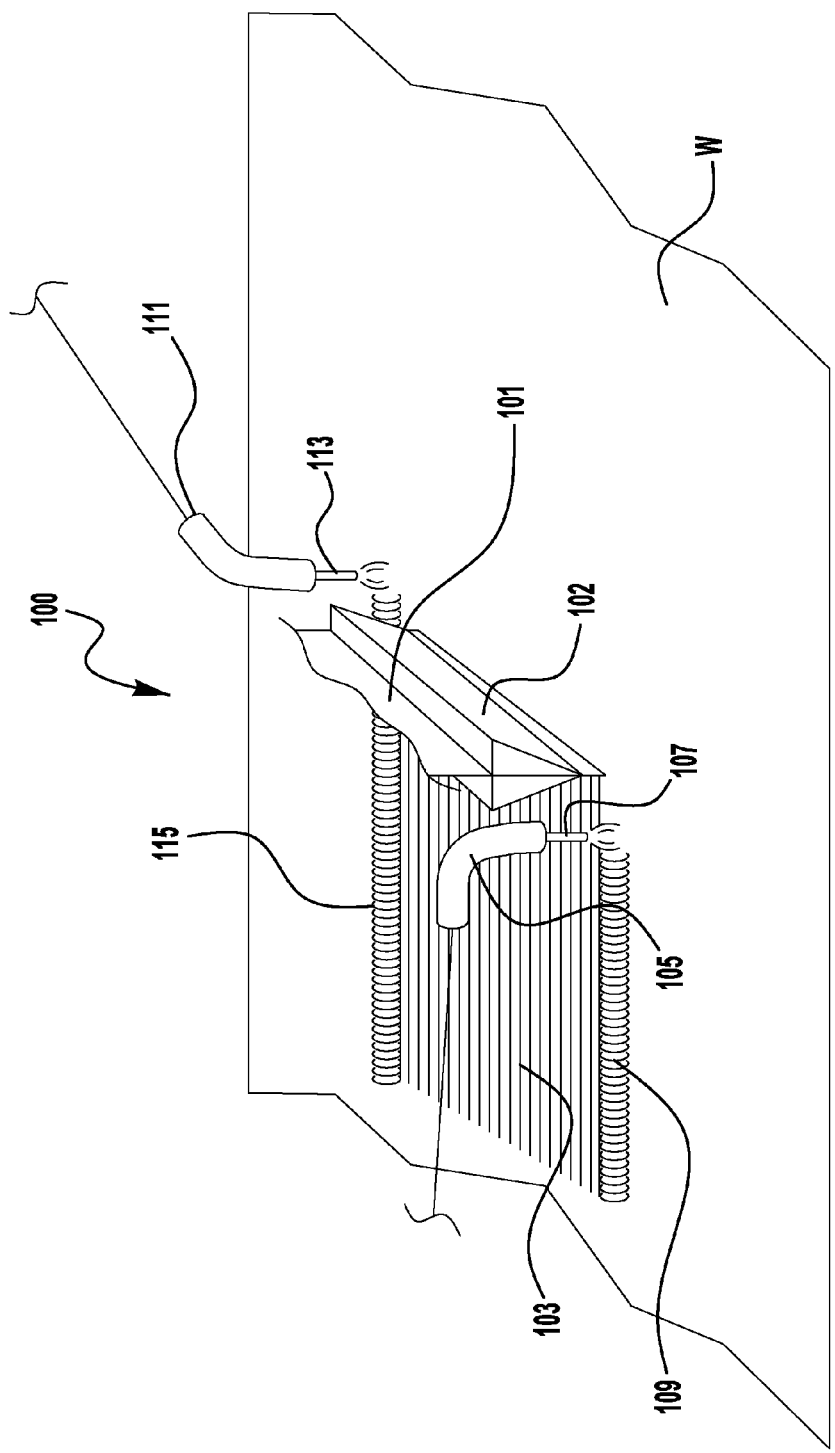
FIG. 1 illustrates a diagrammatical representation of welding with an exemplary embodiment of the present invention.

Exemplary embodiments of the invention will now be described below by reference to the attached Figures. The described exemplary embodiments are intended to assist the understanding of the invention, and are not intended to limit the scope of the invention in any way. Like reference numerals refer to like elements throughout.

FIGS. 1 and 2A-2C diagrammatical representations of welding with an exemplary embodiment of the present invention. In embodiments of the present invention, a strip electrode 101 is employed for example in a cladding operation. In an exemplary embodiment of the present invention the strip electrode is in the range of 30 to 120 mm wide. However, the strip electrode 101 can be wider or narrower depending on the use. In further exemplary embodiments of the present invention the welding process employed is either a submerged arc welding process or an electro-slag welding process. The strip electrode 101 is delivered to the welding operation via a strip feeder (not shown) and current supply jaws 102 which sandwich the strip electrode 101 and deliver the welding current from a power source to the electrode 101. Not shown in FIG. 1 is a welding flux or welding flux delivery system which is often used when welding with strip electrodes, for example in submerged arc welding operations. Because these welding processes and flux delivery systems are well known by those of skill in the art, they will not be discussed in detail herein.

As shown in each of FIGS. 1 and 2A-2C, on either narrow side of the strip electrode 101 is a curtain electrode 107/113. The curtain electrodes 107/113 are deposited using their respective welding torches 105/111 and are deposited simultaneously with the strip electrode 101. That is, during welding each of the strip electrode 101 and the curtain electrodes 107/113 are welded and deposited at the same time. Each of the curtain electrodes 107/113 are typical wire type electrodes (having a circular cross-section) and are positioned a distance from the edges of the strip electrode 101 such that the weld puddles from the curtain electrodes 107/113 contact with the weld puddle of the strip electrode 101 during welding and create a single weld puddle. That is, in a an embodiment of the invention the curtain electrodes 107/113 do not make contact with the strip electrode 101 during the welding/cladding operation. This positioning ensures that the weld beads 109/115 created by the curtain electrodes 107/113 are integrated with the weld bead 103 from the strip electrode 101 creating a single continuous weld bead. If the curtain electrodes 107/113 are positioned too far from the strip electrode 101 the resultant weld puddles separate creating two distinct weld beads. The curtain electrodes 107/113 are electrically isolated from the strip electrode 101, which will be discussed further below.

In an exemplary embodiment of the present invention, the curtain electrodes 107/113 have the same material composition as the strip electrode 101. However, in other exemplary embodiments the material composition of the curtain electrodes 107/113 can be different than the composition of the strip electrode. For example, the curtain electrodes 107/113 can be cored electrodes having a composition comprised of metal powders and wetting agents designed to lower surface tension allowing the deposit to flow easier and flatten out better. Further, flux cored electrodes could be employed with fluxing agents that control the method of transfer metal from the electrode to the puddle. For example, a flux cored curtain electrode can be employed whose core materials promote metal transfer via an arc while the strip electrode 101 is transferring via resistance of the electro slag process. Further, a cored electrode whose core includes chemicals that produce exothermic reactions could increase the heat locally under the curtain wires. For example, the strip electrode 101 can be deposited via a conventional electro-slag process while the flux in the curtain electrodes could react and produce further heat to control and increase the heat at the edges of the deposit thus insuring good penetration and adherence to the previous adjacent clad pass. Thus, by employing curtain electrodes with specific chemical characteristics different than those in the strip electrode 101, the heat and penetration pattern can be manipulated to produce the desired result of a wider clad deposit with good penetration into a previous adjacent bead. Of course, the present invention is not limited to the use of the examples stated above and the use of other electrodes and transferred methodologies can be employed to achieve the desired weld properties.

When welding with further embodiments of the present invention, the same welding process being employed by the strip electrode is also being employed by the curtain electrodes. For example, if submerged arc welding is being employed by the strip electrode 101, the curtain electrodes are employing the same process. The same is true if electro-slag welding is being employed.

In the embodiments shown in FIGS. 1 and 2A-2C, there are at least two curtain electrodes 107/113 shown. However, in other exemplary embodiments only a single electrode 107 or 113 can be used on only one side of the strip electrode 101. Further, during welding both or either one of the curtain electrodes 107 and 113 can be turned off and back on as desired during the welding process.

Figure 2A:
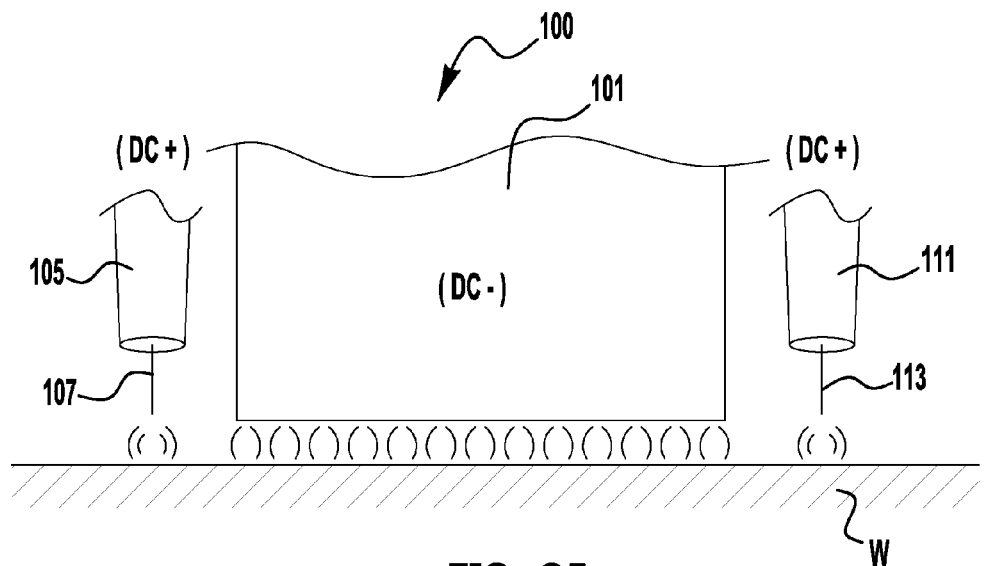
FIGS. 2A, 2B and 2C illustrate other diagrammatical representations of welding with exemplary embodiments of the present invention.
Figure 2B:
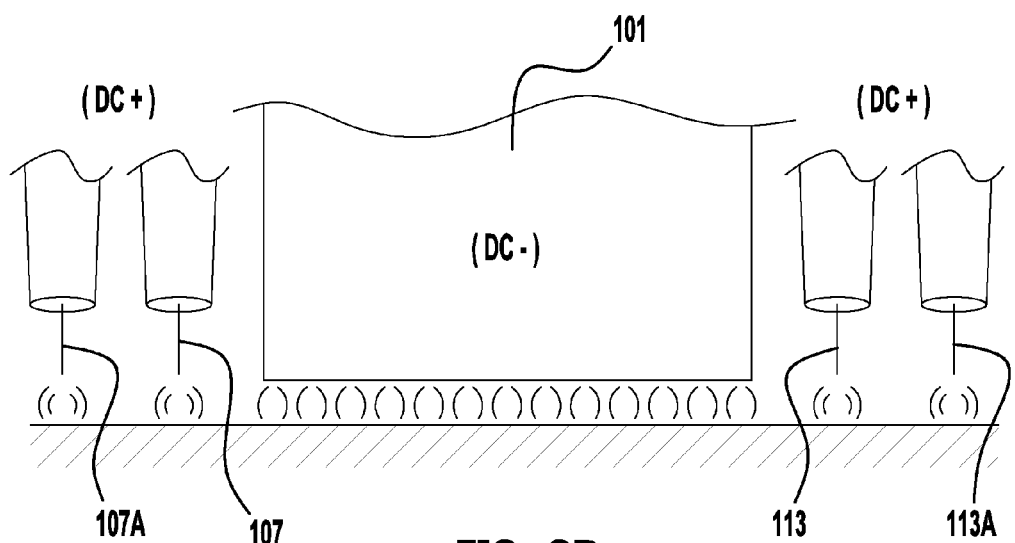

Further, in other exemplary embodiments of the present invention, there is more than one curtain electrode on either side of the strip electrode 101. Specifically, as shown in FIG. 2B, there can be more than one curtain electrode on either side of the strip electrode 101. As shown in this figure, there are two curtain electrodes 107/107A and 113/113A on either side of the strip electrode. This serves to further widen the weld puddle. Further, such an embodiment further increases the magnetic field generated by the curtain electrodes to further negate some of the magnetic forces generated by the strip electrode 101. Such an embodiment increases the magnetic fields at the curtain electrodes without over-penetrating the work piece, which could come from using a single overly-large curtain electrode. It is further noted that embodiments of the present invention are not limited to two curtain electrodes on either side of the strip electrode 101. More than two electrodes per side can also be used.

The use of the curtain electrodes 107/113 increases the width of the overall weld bead being created during the welding process. Thus, the overall deposition rate for a given strip electrode 101 width is increased. Further, the use of the curtain electrodes also aids in addressing the penetration problem described above. Specifically, the use of the curtain electrodes 107/113 aids in ensuring that the edges of the strip electrode 101 sufficiently penetrate the work piece W to achieve a proper weld. Further, the increased penetration provided by the use of the curtain electrodes 107/113 aids in ensuring proper penetration into adjacent weld beads. Again, as stated above, with existing strip electrode welding techniques there can be insufficient penetration between adjacent strip electrode weld beads (in subsequent passes). However, by using the curtain electrodes 107/113 embodiments of the present invention ensures that subsequent adjacent passes have sufficient edge penetration to create a uniform weld bead. Thus, for example when cladding the cladding surface is continuous and has the desired surface integrity. Additionally, by controlling the wire feed speed of the curtain electrodes at the edge of the strip electrode 101 the amount of additional cladding metal (for example) at the edges of the strip electrode 101 can be controlled. In exemplary embodiments, the wire feed speed of the curtain electrodes 107/113 is controlled independently of the strip electrode 101, and in some exemplary embodiments the wire feed speed of the curtain electrodes 107/113 is different from the wire feed speed of the strip electrode 101.

Figure 2C:
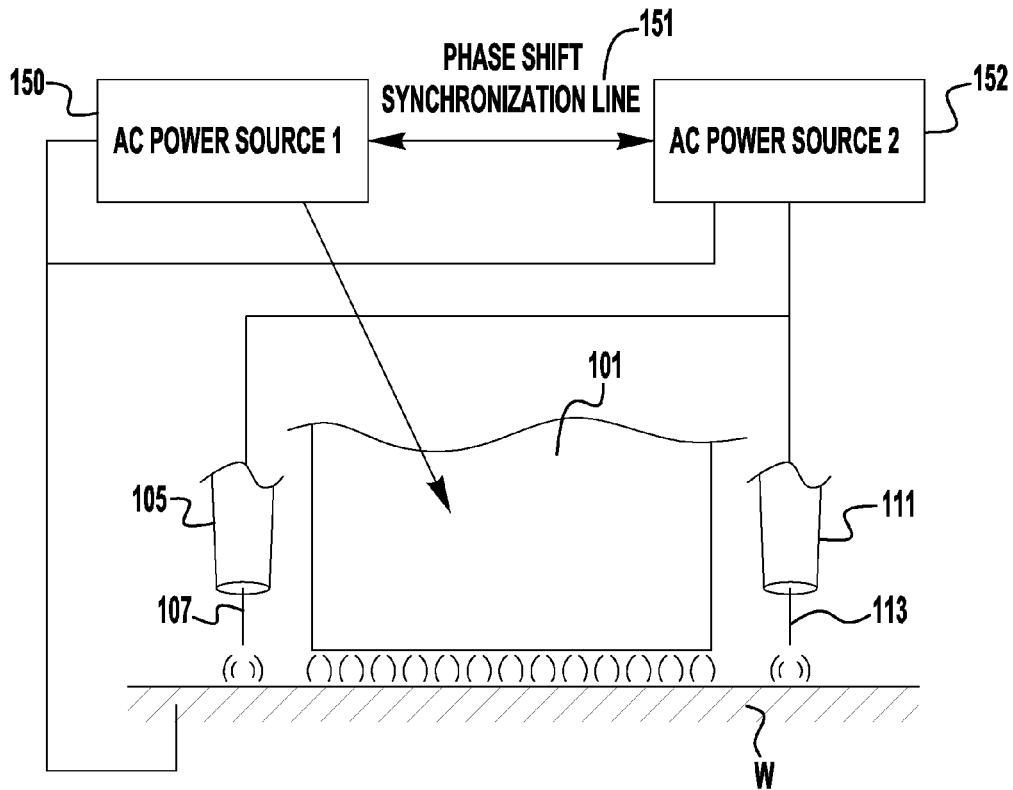
Figure 2C:
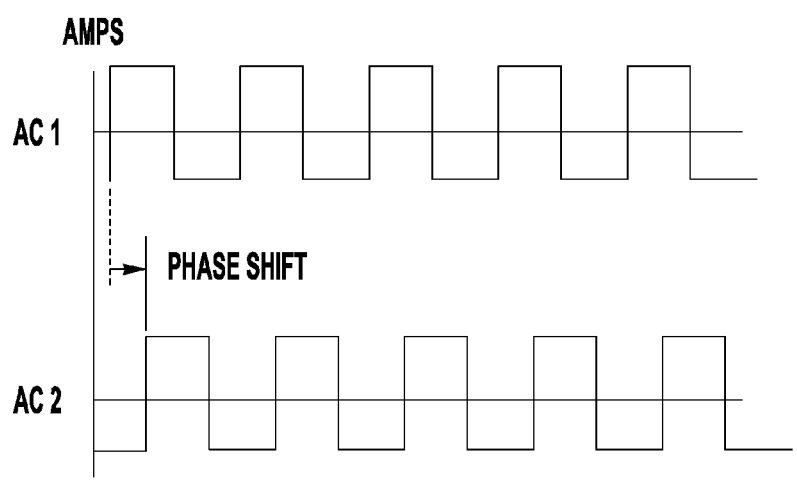

In addition to ensuring sufficient penetration of the weld bead at the edges of the strip electrode 101 and increasing the width of the weld bead, embodiments of the present invention can be employed to control the weld puddle of the strip electrode 101. As discussed above, when welding with strip electrodes in a conventional manner the magnetic forces during welding can cause the weld puddle to pool or collect at the center of the strip, thus causing insufficient weld bead creation at the ends of the strip electrode weld bead 103. Embodiments of the present invention can be used to level the weld puddle, thus creating a more uniform weld bead. This is accomplished by phase relating the welding waveform of curtain electrodes 107/113 with the welding waveform of the strip electrode 101. Specifically, as shown in FIG. 2A/2B, when welding with an electro-slag welding process the curtain wires 107/113 are to have an opposite polarity than the strip electrode 101. As shown in FIG. 2A, the strip electrode 101 is welded with a negative polarity while each of the curtain electrodes has a parallel positive polarity. Similarly, when welding with a submerged arc welding process the welding waveform of the curtain electrodes 107/113 is phased out of phase of the waveform used for the strip electrode 101. An exemplary embodiment of this is shown in FIG. 2C. In this embodiment, two AC power sources 150 and 152 are shown, where the first AC power source 150 supplies a first AC welding waveform to the strip electrode 101 and the second AC power source supplies a second AC welding waveform to the curtain electrodes 107/113. In the exemplary embodiment shown, a phase shift synchronization line 151 is provided between the two power sources 150/152 which ensures that the AC waveform provided by the second power source 152 is out-of-phase with the AC waveform provided by the first power source 150. (This is depicted in the lower portion of the Figure). In the exemplary embodiment shown in FIG. 2C the phase shift is 90 degrees. However, other embodiments of the present invention may employ different phase shifts. For example, the phase shift may be greater than 90 degrees. In any event, the phase shift should be selected to obtain the desired performance from the curtain electrodes 107/113 relative to the strip electrode 101. In the exemplary embodiment shown, a phase shift synchronization line 151 is employed to ensure that the proper phase shift is achieved. The phase shift synchronization line 151 can be a synchronization line dedicated for real time synchronization between the first 150 and the second 152 power supplies, or can be the input power phase shift of three phase power. Further, in other exemplary embodiments the phase shift can be achieved and controlled by various other known methods, such as a dedicated welding controller, which can either be separated from or integral to one or both of the power sources 150/152.

For each of the above described welding processes the phasing of the curtain electrodes 107/113 with the strip electrode 101 allows the curtain electrodes 107/113 to generate their own respective magnetic fields which counteract some of the magnetic forces generated by the strip electrode 101, including those generated at the edges of the strip electrode 101. This pulling force prevents the weld puddle from pooling at the center of the strip 101 and thus causes the weld bead 103 of the strip electrode 101 to be more uniform. Adding to this benefit is, of course, the further benefits described above of increasing the overall width of the collective weld bead and improved the weld penetration at the edges of the strip electrode 101.

Therefore, it has been discovered that by welding with at least one curtain electrode adjacent to the edge of a strip electrode a number of benefits can be achieved as described above.

Although FIGS. 1 and 2A show a single strip electrode 101 being employed with two curtain electrodes 107/113 the present invention is not limited to this configuration. Specifically, it is contemplated that additional strip electrodes and curtain electrodes cans be employed to further widen the weld bead being created, such as shown in FIG. 2B. For example, it is contemplated that an additional strip electrode 101 and curtain electrode can be positioned adjacent to one of the curtain electrodes 107/113 further increasing the width of the weld bead created.

In exemplary embodiments of the present invention the curtain electrodes 107/113 are of the same diameter. However, the present invention is not limited to this as the relative diameters of the curtain electrodes 107/113 can be different from each other. For example, the diameter of the curtain electrodes 107/113 can be used to determine the depth of penetration at the edges of the strip electrode 101. That is, the larger the diameter of the electrode 107/113 the deeper the penetration of the weld. Further, the depth of penetration at the edges of the strip electrode 101 can be controlled by the proximity of the curtain electrodes 107/113 to the strip electrode 101. Thus, in exemplary embodiments of the present invention, the distance between the curtain electrodes 107/113 and the strip electrode 101 can be changed during the welding process. This can be accomplished by using any mechanical system capable of changing the relative location of the curtain electrodes 107/113 relative to the strip electrode 101. For example, a gear and track system can be employed. The relative location of the electrodes can be changed either prior to, or during the welding operation.

In another exemplary embodiment, magnetic arc control can be employed to aid in controlling the strip electrode weld puddle. However, because those skilled in the art are familiar with such methodologies, this technology need not be described in detail herein.

Figure 3:
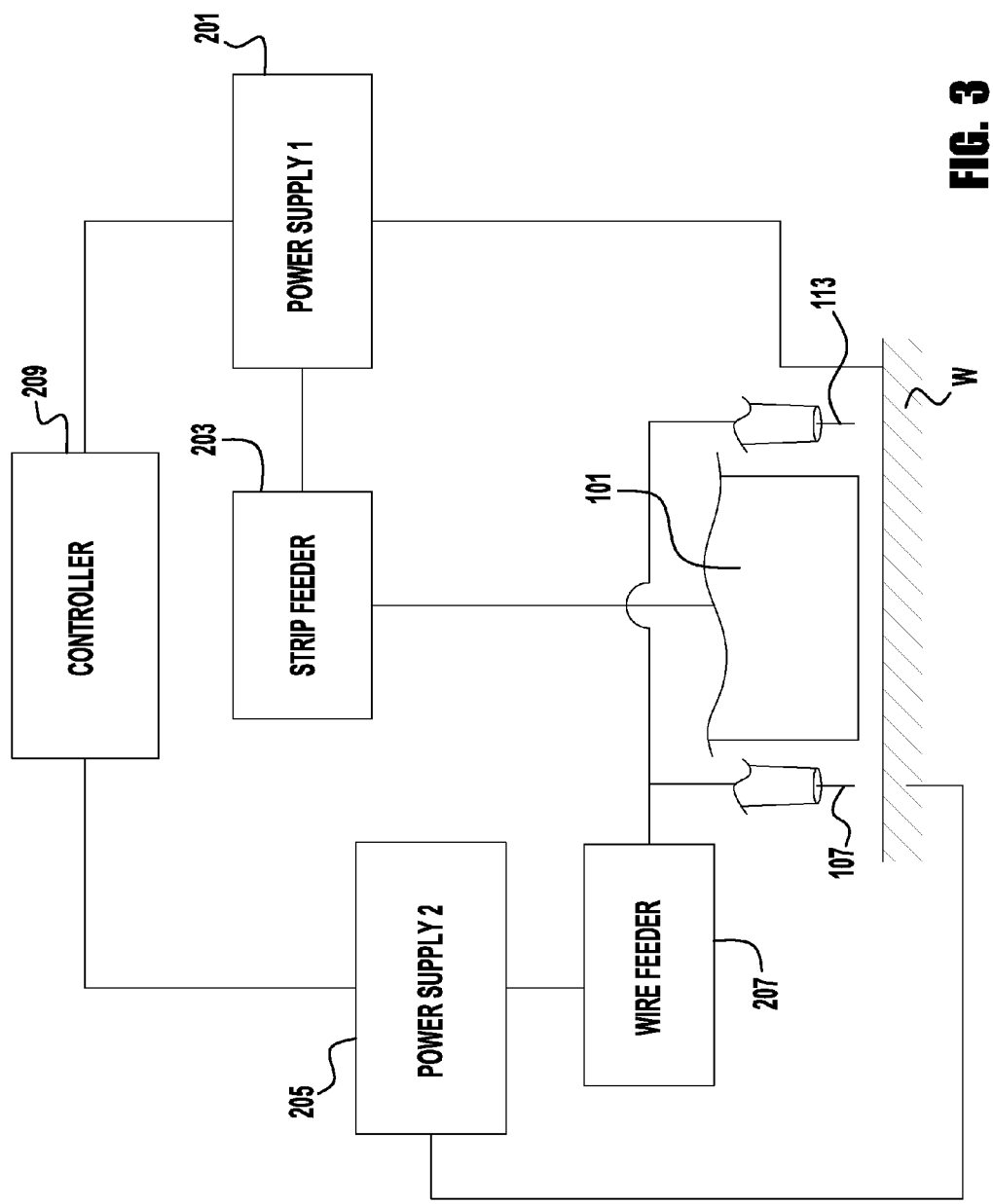
FIG. 3 illustrates a diagrammatical representation of a welding system in accordance with an exemplary embodiment of the present invention.

Turning now to FIG. 3, a welding system 200 in accordance with an exemplary embodiment of the present invention is shown. The welding system contains a first welding power supply 201 and a second welding power supply 203. The first welding power supply 201 provides a first welding waveform to a strip electrode feeder 203 which is feeding the strip electrode 101 to the weld. The second power supply 205 provides a second welding waveform to the curtain electrodes 107/113, through the wire feeder 207. Although a single wire feeder 207 is shown more than one wire feeder can be employed. Additionally, the wire feeder 207 can be a dual type wire feeder which is capable of feeding at least two electrodes at one time. Further, although a single power supply 205 is shown for both electrodes 107/113, it is also contemplated that a single power supply can be utilized with each electrode 107/113, respectively.

Further, in the exemplary embodiment shown in FIG. 3, a welding controller 209 is shown. The controller 209 controls the operation of the power supplies 201 and 205 to ensure that the power supplies 201/205 operate as desired. For example, in a submerged arc welding operation the controller 209 ensures that the power supplies 201/205 are operating such that the welding waveform for the curtain electrodes 107/113 is out of phase with welding waveform for the strip electrode 101. Because welding controllers of the type used to control the operation of more than one power supply are known by those of the skill in the art the structure and operation of the controller 209 will not be described herein in detail. Further, in another exemplary embodiment, the controller 209 can be integral to one of the welding power supplies 201/205. Specifically, the control electronics of one of the power supplies 201/205 can control and monitor the operation of the other of the power supplies 201/205 to ensure a proper welding operation is achieved. It is not required that a separate controller 209 be employed. During operation, the controller 209 can stop and start the welding with the curtain electrodes 107/113 as needed. Further, as discussed above, the electrodes 107/113 are positionable relative to the sides of the strip electrode. Specifically, the locations of the curtain electrodes 107/113 can be changed relative to the sides of the strip electrode 101, either prior to or during welding.

When welding or cladding with various embodiments of the present invention, there are a number of variables which can be controlled and optimized to provide a desired weld. For example, such variables include: the diameter and composition of the curtain electrodes, the size and composition of the strip electrode, the transfer processes being employed for the strip and curtain electrodes, the feed speed of the respective electrodes, the polarity and/or duty cycle of the welding waveforms employed.

It is noted that the present invention is not limited by the type of curtain or strip electrodes to be utilized or the type of welding operation which can be performed, but can be used in many different types of welding operations with many different types of welding electrodes and electrode combinations.

While the invention has been particularly shown and described with reference to exemplary embodiments thereof, the invention is not limited to these embodiments. It will be understood by those of ordinary skill in the art that various changes in form and details may be made therein without departing from the spirit and scope of the invention as defined by the following claims.

What is claimed is:

1. A welding system, comprising:
 a strip electrode and a first welding power supply which provides a first welding waveform to the strip electrode for welding a work piece; and
 at least one curtain electrode and second welding power supply which provides a second welding waveform to said at least one curtain electrode for welding said work piece;
 wherein said at least one curtain electrode is positioned adjacent to a side of said strip electrode during welding.

2. The welding system of claim 1, wherein a second curtain electrode is positioned adjacent to another side of said strip electrode during welding.

3. The welding system of claim 1, wherein said at least one curtain electrode is positioned adjacent to said side by a distance such that a weld bead from said at least one curtain electrode is integrated with a weld bead of said strip electrode.

4. The welding system of claim 1, wherein said at least one curtain electrode has a different composition than said strip electrode.

5. The welding system of claim 1, wherein said first welding waveform is one of an electro-slag and submerged arc welding waveform and said second welding waveform is different from said first welding waveform.

6. The welding system of claim 1, wherein the at least one curtain electrode includes at least two curtain electrodes positioned adjacent said side during said welding.

7. The welding system of claim 1, Wherein said first welding waveform is an electroslag welding waveform and said second welding waveform has an opposite polarity than said first welding waveform.

8. The welding system of claim 1, wherein said first welding waveform is an AC welding waveform and said second welding waveform is phase shifted to be out of phase with said first welding waveform.

9. The welding system of claim 2, wherein said at least one curtain electrode has at least one of a different diameter and material composition than said second curtain electrode.

* * * * *